(12) United States Patent
Formica et al.

(10) Patent No.: US 6,344,133 B1
(45) Date of Patent: Feb. 5, 2002

(54) PROCESS FOR OPERATING AN ELECTROCHEMICAL MEASURING CELL

(75) Inventors: Philip Michael Formica; Ingo Kaneblei, both of Lübeck (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/313,825

(22) Filed: May 18, 1999

(30) Foreign Application Priority Data

Nov. 6, 1998 (DE) ......................................... 198 51 164

(51) Int. Cl.⁷ ............................................ G01N 27/404
(52) U.S. Cl. ..................... 205/775; 204/400; 204/402; 204/415; 205/782.5
(58) Field of Search ................ 204/400, 402, 204/415, 431, 432; 205/775, 782, 782.5, 783

(56) References Cited

U.S. PATENT DOCUMENTS

| | | | | |
|---|---|---|---|---|
| 3,406,109 A | * | 10/1968 | Molloy | 204/415 |
| 4,077,861 A | * | 3/1978 | Laver | 204/402 |
| 4,556,472 A | * | 12/1985 | Langdon | 204/415 |
| 4,735,691 A | * | 4/1988 | Green et al. | 204/415 |
| 4,897,162 A | * | 1/1990 | Lewandowski et al. | 204/415 |
| 5,254,226 A | * | 10/1993 | Williams et al. | 204/402 |
| 5,611,908 A | | 3/1997 | Matthiessen et al. | |
| 5,653,863 A | * | 8/1997 | Genshaw et al. | 204/402 |

FOREIGN PATENT DOCUMENTS

| | | |
|---|---|---|
| DE | 38 09 107 C2 | 9/1989 |
| DE | 44 45 948 C2 | 6/1996 |

* cited by examiner

*Primary Examiner*—T. Tung
(74) *Attorney, Agent, or Firm*—McGlew and Tuttle, P.C.

(57) ABSTRACT

A process for operating an electrochemical measuring cell (1) is described, with which it is possible to carry out gas concentration measurements already shortly after switching on the measuring cell (1). The process includes the steps that potential voltage pulses are applied to the measuring cell (1) in a state of readiness of the measuring cell (1), in which the potential voltage is switched off. A system and device are also described.

19 Claims, 3 Drawing Sheets

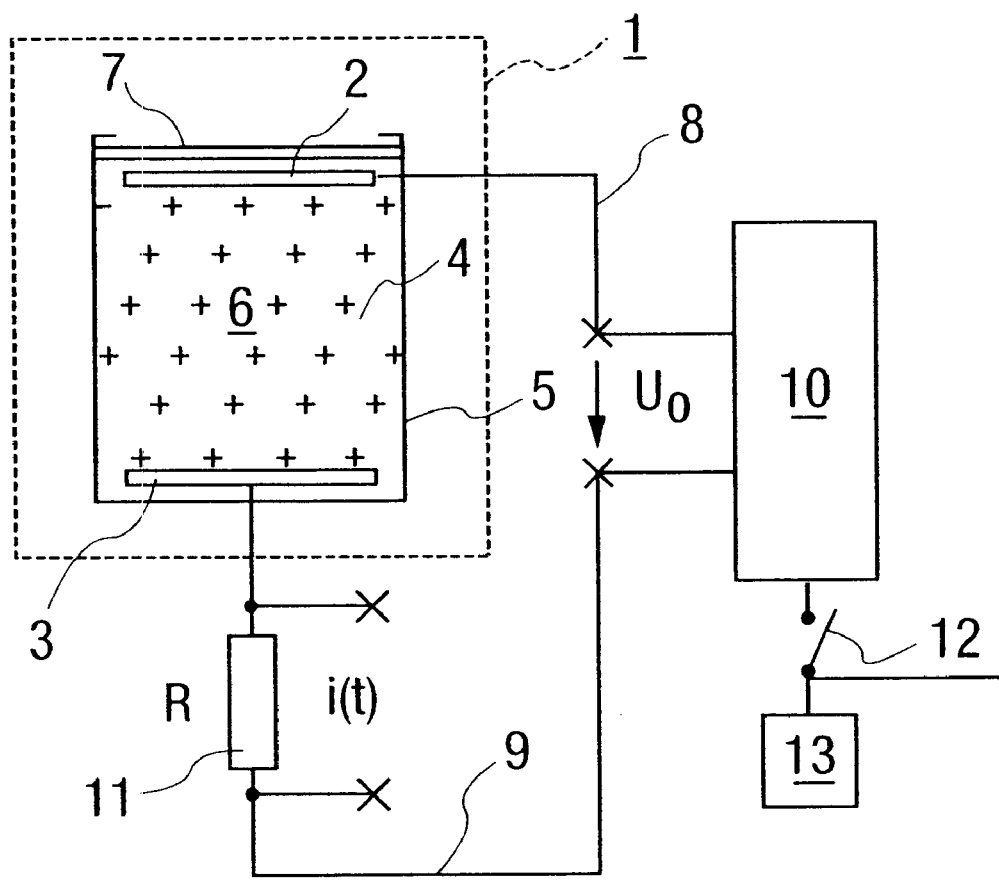
Fig. 3
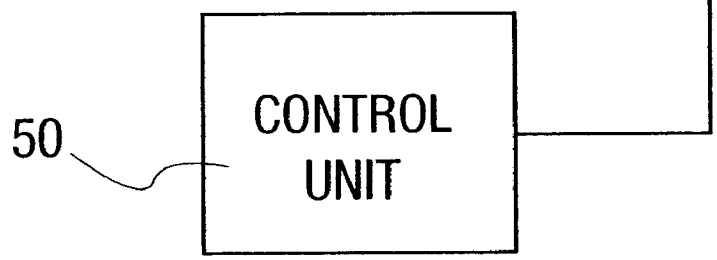

PROCESS FOR OPERATING AN ELECTROCHEMICAL MEASURING CELL

FIELD OF THE INVENTION

The present invention pertains to a process operating an electrochemical measuring cell, which is connected to a potential voltage source with a pulse generator to generate potential voltage pulses and to which at least one potential voltage $U_0$ supplied by the potential voltage source is applied in the measuring operation.

BACKGROUND OF THE INVENTION

A process for automatically checking the characteristics of an electrochemical gas-measuring cell, in which different voltage pulse trains are applied to the gas-measuring cell which is in the measuring operation, has been known from DE 38 09 107 C1. Changes in the sensitivity of the gas-measuring cell can be inferred from a comparison of the impressed voltage pulses with the corresponding current pulses. Thus, it can be determined, e.g., during the measuring operation whether the sensitivity has changed briefly or over the long term.

A process for improving the break-in characteristic of electrochemical measuring cells has been known from DE 44 45 948 C2; this process is based on setting the potential voltage at an increased value after switching on for a predetermined length of time so that the sensor current resulting from the increased potential voltage will come close to the stationary sensor rest current after a short time.

The prior-art process has the drawback that measurement cannot be begun immediately after switching on the electrochemical measuring cell, because stationary operating conditions must first be established. In addition, the break-in time of an electrochemical measuring cell depends on the concentration of the gas to be detected in the environment of the measuring cell. If, e.g., the measuring cell is exposed to the gas to be detected without potential voltage applied, an electrochemical reaction, which leads to a change in potential at the electrodes, takes place within the measuring cell because of diffusion processes. This potential shift must first be eliminated after switching on.

SUMMARY AND OBJECTS OF THE INVENTION

The primary object of the present invention is to provide a process and system for operating an electrochemical measuring cell, with which it is possible to carry out gas concentration measurements just a short time after switching on the operating potential voltage.

According to the invention a process for operating an electrochemical measuring cell is provided as well as a system and device for accomplishing the process. The measuring cell is connected to a potential voltage source with a pulse generator to generate potential voltage pulses and to which at least one potential voltage $U_0$ supplied by the potential voltage source is applied in the measuring operation. The potential voltage pulses are applied in steps to the said measuring cell in a state of readiness of the said measuring cell, in which the potential voltage $U_0$ is switched off.

It has been surprisingly found that an electrochemical measuring cell, to which potential voltage pulses are applied at regular intervals in the state of readiness, in which the potential voltage is switched off, can be used for measuring purposes almost without delay after the potential voltage necessary for the measuring operation has been applied. The pulsed operation during the state of readiness is especially significant for portable, battery-operated measuring instruments, because the readiness to operate can thus be maintained for a long time without excessive power consumption. Only about 4% of the power needed during the measuring operation is needed in the state of readiness compared with the measuring operation with constant potential voltage applied.

It is especially advantageous for the potential voltage pulses to have the amplitude of the potential voltage occurring during operation. Readiness of the measuring cell to operate can thus be achieved in an especially short time after switching on the potential voltage.

The potential voltage pulses are selected to be such that the duration of the interpulse period is between 1 minute and 60 minutes.

Preferred values for the pulse length are between 8 sec and 30 sec.

It is advantageous to select the ratio of the pulse length to the duration of the interpulse period between 1:10 and 1:100.

The ratio of the pulse length to the duration of the interpulse period to be set depends on the concentration of the gas component to be detected, which occurs during the state of readiness. Since correspondingly more gas molecules enter the interior of the measuring cell due to diffusion processes at a high gas concentration, a correspondingly high ratio of the pulse length to the duration of the interpulse period shall be set, i.e., a value in the direction of 1:10.

It is especially advantageous for the ratio of the pulse length to the duration of the interpulse period during the state of readiness to be adjusted to the gas concentration by performing gas concentration measurements at predetermined intervals in the course of the state of the readiness and by setting the ratio of the pulse length to the duration of the interpulse period corresponding to the gas concentration measured.

Exemplary embodiments of the present invention are shown in the drawings and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a schematic view of an electrochemical measuring cell connected to a potentiostat and with a control device;

DESCRIPTION OF THE PREFERRED EMBODIMENT

Figure 1:
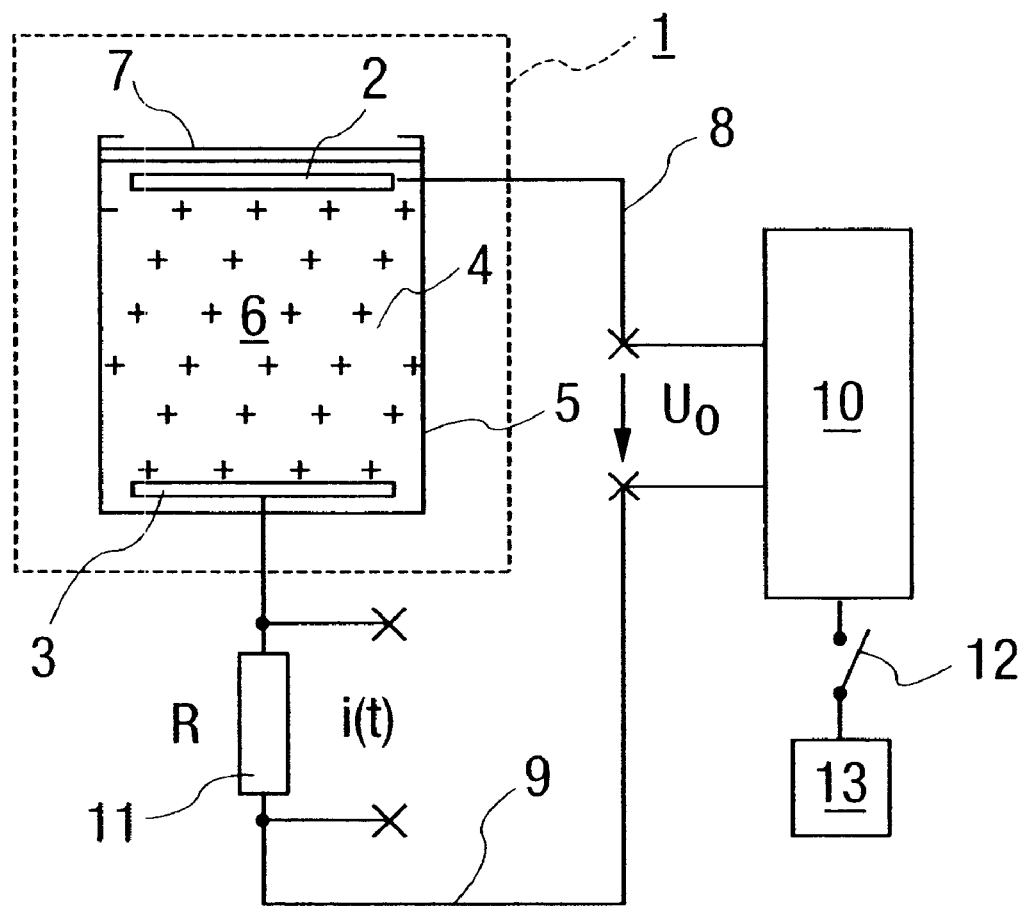
FIG. 1 is a schematic view of an electrochemical measuring cell connected to a potentiostat.

Referring to the drawings in particular, FIG. 1 schematically shows the system components according to the invention, which include an electrochemical measuring cell 1, containing a measuring electrode 2 and a counterelectrode 3. The system components are arranged in an electrolyte space 4 of a measuring cell housing 5. The measuring cell housing 5 is filled with an electrolyte 6 and is closed with a permeable membrane 7 toward the gas to be detected. The electrodes 2, 3 are connected via lines 8, 9 to a potentiostat 10, with which a potential voltage $U_0$ is applied to the electrodes 2, 3. The sensor current i(t) is picked off as a voltage drop over a precision resistor 11 in the line 9. The potentiostat 10 is connected via a switch 12 as a pulse generator to a power supply unit 13.

Figure 2:
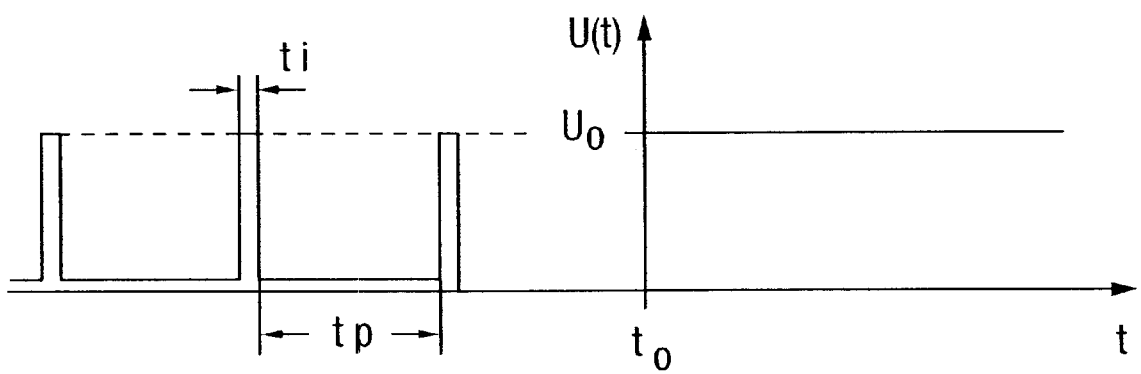
FIG. 2 is a schematic showing of a train of potential voltage pulses.

FIG. 2 illustrates a diagram or the curve of the potential voltage $U_0$ as a function of the time t. The state of readiness of the electrochemical measuring cell 1 is present for times t shorter than $t_0$, while the measurement is begun at time t=$t_0$. In the state of readiness, the switch 12, FIG. 1, is closed only during the pulse lengths to and it is open during the duration of the interpulse period $t_p$. Potential voltage pulses with the amplitude of the operating potential voltage $U_0$ are generated with the opening and closing of the switch 12. The switch 12 is continuously closed during the measuring operation, so that the potential voltage $U_0$ is present at the electrodes 2, 3 and the percentage of the gas component to be detected in the gas sample can be determined from the sensor current i(t).

The device and system according to the present invention operates as follows.

Potential voltage pulses of the amplitude $U_0$ are applied to the electrodes 2, 3 of the electrochemical measuring cell 1 during the state of readiness in order to prepare the measuring cell 1 for a possible use. A possible poisoning of the measuring cell 1 due to the accumulation of gases within the electrolyte space 4 is prevented by the pulsed operation in the state of readiness (readiness state). The duration of the interpulse period $t_p$ between two pulses is 10 minutes, and the pulse length $t_i$ is 15 sec. The measuring operation (measuring state) is started at time t =$t_0$ to by closing the switch 12, and the potential voltage $U_0$ is continuously present at the electrodes 2, 3. The gas concentration measurement can be begun with the beginning of the measuring operation after a short break-in time due to the pulsed operation during the state of readiness.

A control unit 50 may be provided as shown in FIG. 3. The control unit 50 may be used to switch between an off state, a readiness state and a measuring operation state. The control element 50 can also provide the short break-in time prior to measuring, which may be required due to the pulsed operation during the state of readiness.

While specific embodiments of the invention have been shown and described in detail to illustrate the application of the principles of the invention, it will be understood that the invention may be embodied otherwise without departing from such principles.

What is claimed is:

1. A process for operating an electrochemical measuring cell. the process comprising the steps of:

providing an electrochemical cell with a measuring cell housing filled with an electrolyte and closed with a gas permeable membrane and having a measuring electrode and a counterelectrode;

connecting the measuring electrode and the counterelectrode to a potential voltage source with a pulse generator;

applying a substantially constant measuring potential voltage $U_0$ to the cell, supplied by the potential voltage source in a gas measuring operation;

generating readiness potential voltage pulses in a gas cell readiness operation using the potential voltage source and applying the readiness potential voltage pulses to the measuring electrode and the counterelectrode to provide a state of readiness of the cell during said gas cell readiness operation each of said pulses including a potential voltage pulse amplitude applied for a pulse period with successive pulse periods separated by an interpulse period during which no potential is applied to said measuring electrode and the counterelectrode.

2. The process in accordance with claim 1, wherein the readiness potential voltage pulses have the amplitude of the measuring potential voltage $U_0$.

3. The process in accordance with claim 2, wherein the readiness potential voltage pulses are selected such that an interpulse period $t_p$ between 1 minute and 60 minutes is provided.

4. The process in accordance with claim 1, wherein the readiness potential voltage pulses are selected such that an interpulse period $t_p$ between 1 minute and 60 minutes is provided.

5. The process in accordance with claim 1, wherein a pulse length $t_i$ to duration of interpulse period $t_p$ ratio ranging from 1:10 to 1:100 is set for the readiness potential voltage pulses.

6. The process in accordance with claim 5, wherein gas concentration measurements are carried out and the ratio of the pulse length $t_i$ to the duration of the interpulse period $t_p$ is set corresponding to the gas concentration measured.

7. A electrochemical measuring cell system, comprising:
an electrochemical cell;
a potential voltage source connected to said cell;
a pulse generator; and
a control for establishing a measuring state with a potential voltage $U_0$ applied to the cell and supplied by the potential voltage source in a measuring operation and establishing a readiness state with potential voltage pulses generated by the potential voltage source and applied to the cell in the state of readiness of the cell, in which the potential voltage is not applied between the pulses.

8. The system in accordance with claim 7, wherein the potential voltage pulses have the amplitude of the potential voltage $U_0$.

9. The system in accordance with claim 7, wherein the potential voltage pulses are selected such that an interpulse period $t_p$ between 1 minute and 60 minutes is provided:
a pulse length $t_i$ to duration of interpulse period $t_p$ ratio ranging from 1:10 to 1:100 is set for potential voltage pulses.

10. The system in accordance with claim 7, wherein gas concentration measurements are carried out and a ratio of pulse length $t_i$ to interpulse period $t_p$ is set corresponding to the gas concentration measured.

11. A measuring cell system in accordance with claim 7, further comprising:
a measuring electrode conductive line connected to said measuring electrode;
a counter electrode conductive line connected to said counter electrode;
a resistor provided in series in said counter electrode conductive line;
tap lines for measuring a sensor current by providing an indication of the voltage drop across said resistor;
a potentiostat connected to said measuring electrode conductive line and said counter electrode conductive line;
a switch connecting said potential voltage source to said potentiostat, said control unit controlling said switch to establish said measuring state with said potential voltage $U_0$ applied to the cell and to establish said readiness state with said potential voltage pulses applied to the cell.

12. A process for operating an electrochemical measuring cell, the process comprising the steps of:

providing an electrochemical cell system with an electrochemical cell having a measuring cell housing filled with an electrolyte and closed with a gas permeable membrane and having a measuring electrode and a counterelectrode, a potential voltage source connected to the cell, a pulse generator and a control;

connecting the measuring electrode and a counterelectrode to the potential voltage source with the pulse generator;

establishing a measuring state with the cell by applying a substantially constant measuring potential voltage $U_0$ to the measuring electrode and a counterelectrode, the measuring potential voltage being supplied by the potential voltage source;

establishing an off state with the cell with no measuring potential voltage applied to the measuring electrode and the counterelectrode;

establishing a readiness state with the cell by generating potential voltage pulses with the potential voltage source and applying the potential voltage pulses to the measuring electrode and the counterelectrode, each of the pulses including a potential voltage pulse amplitude applied for a pulse period with each of successive pulse periods separated by an interpulse period during which no measuring potential voltage is applied to the measuring electrode and the counterelectrode.

13. A process in accordance with claim 12, wherein:

the measuring state is established after said readiness state;

the potential voltage pulses are applied substantially periodically;

establishing a measuring state includes measuring a concentration of a gaseous sample.

14. A process in accordance with claim 12, wherein:

the amplitude of the measuring potential voltage and the polarity of the measuring potential voltage are substantially equal to the amplitude of the potential voltage pulses and the polarity of the potential voltage pulses.

15. A process in accordance with claim 12, wherein:

the measuring potential voltage is applied during said measuring state for a period longer than the pulse period.

16. A process in accordance with claim 12, wherein:

measurements of the sample are carried out at predetermined intervals and a ratio of pulse length $t_i$ to interpulse period $t_p$ is varied corresponding to said measurements.

17. A process for measuring gas concentration of a gas sample, the process comprising the steps of:

exposing an electrochemical cell to a gas sample, the electrochemical cell having a measuring cell housing filled with an electrolyte and closed with a gas permeable membrane and having a measuring electrode and a counterelectrode;

applying a plurality of voltage pulses to the cell to form a readiness state of the cell;

applying a substantially constant voltage to the cell to form a measuring state of the cell; and measuring the sample with said cell in said measuring state.

18. A process in accordance with claim 17, wherein:

the measuring state is established after said readiness state; and the potential voltage pulses are applied substantially periodically;

the amplitude of the measuring potential voltage and the polarity of the measuring potential voltage are substantially equal to the amplitude of the potential voltage pulses and the polarity of the potential voltage pulses; and the measuring potential voltage is applied during said measuring state for a period longer than the pulse period.

19. A process in accordance with claim 17, wherein:

measurements of the sample are carried out at predetermined intervals and a ratio of pulse length $t_i$ to interpulse period $t_p$ is varied corresponding to said measurements.

* * * * *